(12) United States Patent
Nadeau

(10) Patent No.: US 9,648,942 B2
(45) Date of Patent: May 16, 2017

(54) TOOTHBRUSH

(71) Applicant: Regents of the University of Minnesota, Minneapolis, MN (US)

(72) Inventor: Richard Nadeau, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/829,141

(22) Filed: Aug. 18, 2015

(65) Prior Publication Data
US 2016/0051040 A1    Feb. 25, 2016

Related U.S. Application Data

(60) Provisional application No. 62/039,133, filed on Aug. 19, 2014.

(51) Int. Cl.
| | | |
|---|---|---|
| A46B 5/00 | (2006.01) | |
| A46B 7/06 | (2006.01) | |
| A46B 9/04 | (2006.01) | |
| A61C 3/00 | (2006.01) | |

(52) U.S. Cl.
CPC ............ *A46B 9/045* (2013.01); *A46B 5/0012* (2013.01); *A46B 5/0025* (2013.01); *A46B 5/0029* (2013.01); *A46B 7/06* (2013.01); *A61C 3/005* (2013.01); *A46B 2200/1066* (2013.01)

(58) Field of Classification Search
CPC ....... A46B 5/0029; A46B 5/0037; A46B 7/06; A46B 9/04; A46B 9/045
See application file for complete search history.

(56) References Cited

U.S. PATENT DOCUMENTS

| | | | |
|---|---|---|---|
| 887,181 A | 5/1908 | Barnes | |
| D41,285 S | 4/1911 | Kress | |
| D44,997 S | 12/1913 | Carroll | |
| 1,417,407 A * | 5/1922 | Novak | A46B 9/045 |
| | | | 15/167.2 |
| 1,421,199 A | 6/1922 | Field | |
| 1,578,074 A * | 3/1926 | Chandler | A46B 7/04 |
| | | | 15/176.4 |
| 1,670,342 A * | 5/1928 | Chandler | A46B 7/04 |
| | | | 15/188 |
| 1,830,995 A * | 11/1931 | Genn | A46B 9/045 |
| | | | 15/167.2 |
| 2,244,615 A | 6/1941 | Garcin | |
| 3,398,421 A * | 8/1968 | Rashbaum | A46B 7/06 |
| | | | 15/110 |
| 3,535,047 A | 10/1970 | Vireno | |

(Continued)

FOREIGN PATENT DOCUMENTS

| | | | |
|---|---|---|---|
| GB | 994392 | * | 6/1965 |
| GB | 2457665 | * | 8/2009 |
| WO | WO 2008/047492 | * | 4/2008 |

*Primary Examiner* — Randall Chin
(74) *Attorney, Agent, or Firm* — Brian D. Kaul; Westman, Champlin & Koehler, P.A.

(57) ABSTRACT

An improved toothbrush is provided. The improved toothbrush includes first and second flexible anchor portions; a plurality of bristles coupled to each of the first and second flexible anchor portions; and a soft pivot bar operably coupled to the flexible anchor portions. A chewing force applied to the pivot bar causes the pivot bar and the first and second flexible anchor portions to compress against a tooth surface to cause a cleaning action.

10 Claims, 9 Drawing Sheets

(56) References Cited

U.S. PATENT DOCUMENTS

| | | | |
|---|---|---|---|
| 5,137,039 A | 8/1992 | Klinkhammer | |
| 5,175,901 A * | 1/1993 | Rabinowitz | A46B 9/045 |
| | | | 15/167.1 |
| 5,228,466 A | 7/1993 | Klinkhammer | |
| 5,305,491 A | 4/1994 | Hegemann | |
| 5,360,025 A | 11/1994 | Klinkhammer | |
| 5,483,722 A | 1/1996 | Scheier et al. | |
| D374,351 S | 10/1996 | van Kempen | |
| 5,669,097 A | 9/1997 | Klinkhammer | |
| 5,842,249 A | 12/1998 | Sato | |
| 5,873,140 A | 2/1999 | Holloway | |
| 6,254,390 B1 | 7/2001 | Wagner | |
| 6,381,794 B1 | 5/2002 | Porper et al. | |
| 6,625,834 B2 | 9/2003 | Dean | |
| 7,036,180 B2 | 5/2006 | Hanlon | |
| 9,173,476 B2 * | 11/2015 | Minano Fernandez | A46B 9/045 |
| 2002/0083539 A1 | 7/2002 | Bella | |
| 2002/0152563 A1 | 10/2002 | Sato | |
| 2002/0157202 A1 | 10/2002 | Hartel | |
| 2003/0126705 A1 | 7/2003 | Hanlon | |
| 2005/0015908 A1 | 1/2005 | Hanlon | |
| 2005/0108842 A1 | 5/2005 | Shunock | |
| 2006/0085933 A1 | 4/2006 | Meyman | |
| 2009/0056045 A1 | 3/2009 | Cho | |
| 2011/0078867 A1 * | 4/2011 | Liangco | A46B 7/02 |
| | | | 15/167.2 |
| 2011/0113576 A1 | 5/2011 | Yankell | |
| 2011/0209299 A1 | 9/2011 | Simovitz | |
| 2013/0067670 A1 | 3/2013 | Liangco | |
| 2013/0333134 A1 | 12/2013 | Herr et al. | |

* cited by examiner

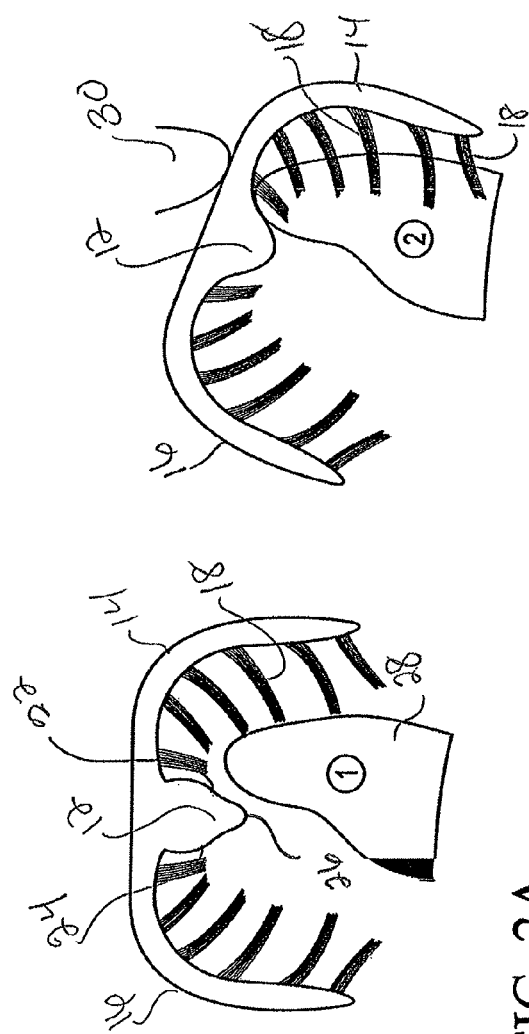
FIG. 2A
FIG. 2B
FIG. 2C

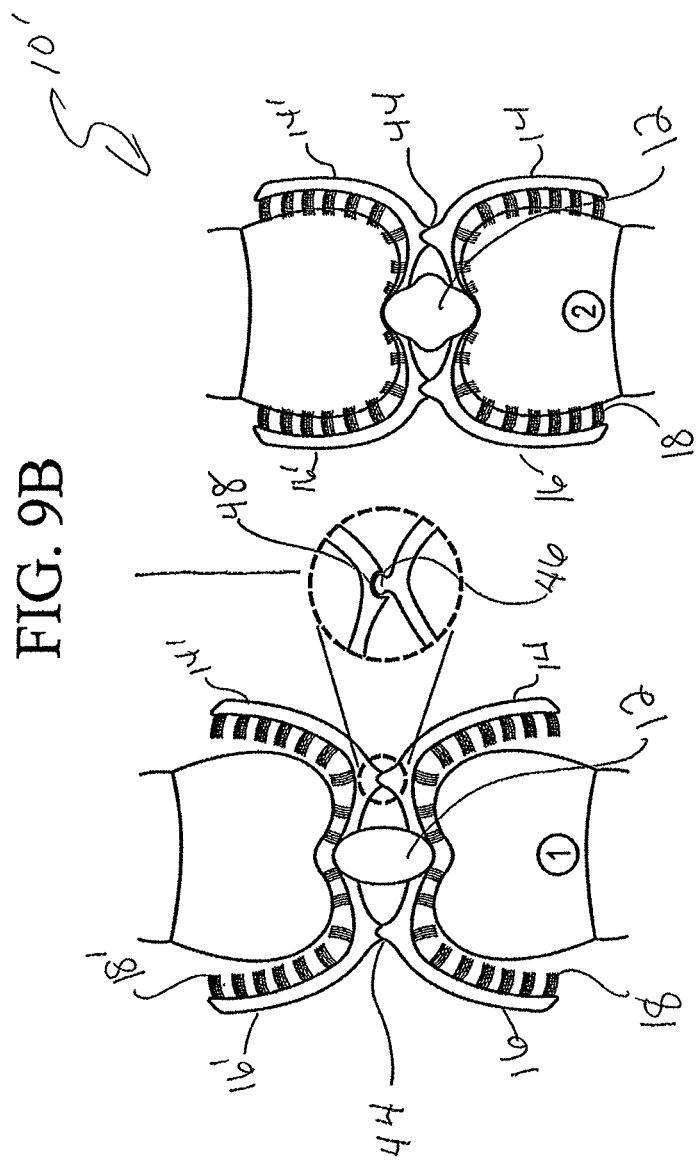

TOOTHBRUSH

CROSS-REFERENCE TO RELATED APPLICATIONS

This application claims the benefit of U.S. Ser. No. 62/039,133, filed on Aug. 19, 2014, the entirety of which is hereby incorporated by reference.

FIELD OF THE INVENTION

The present invention relates generally to a toothbrush with an improved cleaning head. More particularly the present invention relates to a chewable toothbrush having a pliable pivot bar operably coupled to two pliable anchor portions.

BACKGROUND OF THE INVENTION

Toothbrushes are known. Generally a toothbrush is used to clean the teeth by removing plaque and debris from the tooth surfaces. Conventional toothbrushes include a stem for holding by a user, a flat plate-like header and bristles made of synthetic resin implanted on the header in such a manner as to be spaced apart from each other by a given distance. The bristles may be of different lengths or diameters from each other so as to enhance the contact force with the teeth according to the curved surfaces of the teeth. However, the bristles of these conventional toothbrushes are implanted erect on the flat plate-like header, and accordingly, the bristles are not elastically moved in accordance with the shape of the teeth. The resulting contact area between the bristles and the teeth is small, which in turn causes the frictional forces of the bristles against the teeth are not uniformly applied to the tooth surface decreasing the benefits of the cleaning process.

Multi-part wheeled hub designs are known but also have drawbacks. During the brushing process, dentifrice slips through the tufts of bristles and away from the contact between the bristles and the teeth. As a result, the dentifrice often is spread around the mouth greatly reducing the benefits of the cleaning process is greatly reduced.

Another drawback of a multi-part wheeled design is the need for space on the sides of the wheels to mount the hubs. The areas adjacent to the hubs must be free of bristles, as the bristle mounting would interfere with the hub function. Large areas of brush head interior that are devoid of bristles greatly reduce cleaning efficiency of conventional toothbrushes.

Moreover, most conventional toothbrushes do not clean the entire surface of the tooth, especially the buccal and lingual tooth surfaces, without manual manipulation by a user.

Therefore, what is needed is a new and improved toothbrush that addresses the deficiencies of conventional toothbrushes.

BRIEF SUMMARY OF THE INVENTION

The problems associated with conventional toothbrushes are addressed by the toothbrush in accordance with the present invention.

The toothbrush in accordance with the invention is adapted to clean the entire surface of the teeth with a natural chewing motion. The toothbrush include pliable or flexible center pivot bar. The pivot bar guides the brush head into the central groove of the tooth and allows the toothbrush, when chewing force is applied, to pivot back and forth, causing the bristles to contact and clean the entire tooth surface.

The outside of the brush mimics the exact contours of a tooth leading to better adaptation of the brush to the enamel surface. The outer surface of the tooth brush will flex over the tooth's height of contour thereby lightly pressing the bristles against the tooth. The bristles are configured such that when chewing force is applied all surfaces of the teeth are cleaned, i.e. in the grooves, under the gums and under the contact between the teeth. The bristles are configured with multiple bends and various degrees of stiffness allowing them to reach better in susceptible areas to prevent gum disease and cavities. The chewing motion places the bristles into these susceptible areas at right angles.

In certain aspects, the toothbrush in accordance with the invention is designed to clean the entire tooth surface with a natural chewing motion.

In other aspects, the toothbrush according to the invention may include a chewable bristle anchor that enables the user to clean his teeth by chewing on the toothbrush.

In other aspects, the toothbrush in accordance may be supplied as a single-use or multiple-use toothbrush.

In other aspects, the toothbrush in accordance with the invention includes a chewable bristle anchor having an uncompressed shape, a plurality of bristles attached to the bristle anchor, and an optional handle connected to the bristle anchor.

In other aspects, the toothbrush in accordance with the invention includes a soft center pivot bar for positioning the toothbrush on the outer surface of the tooth.

In other aspects, the bristle anchor is configured to compress upon itself in response to application of an external chewing force and to return to its uncompressed shape in response to removal of the external chewing force.

In other aspects, the toothbrush in accordance with the invention includes an optional handle for inserting and extracting the toothbrush from the mouth.

In yet other aspects of the invention, the user may not need to manually manipulate the toothbrush using a traditional brushing motion as with a conventional toothbrush thus making it ideal for individuals with poor dexterity, the elderly, individuals with severe arthritis, special needs patients and children.

BRIEF DESCRIPTION OF THE DRAWINGS

For a better understanding of the invention, and to show how the same may be carried into effect, reference will now be made, by way of example, to the accompanying drawings, in which:

FIGS. 2A-2C are illustrations of an exemplary embodiment of the toothbrush in accordance with the invention depicting the cleaning of a first type of tooth.

FIG. 9A is a front view of the toothbrush of FIG. 8 depicting the articulating motion of a joint.

FIG. 9B is an enlargement of the articulating joint of FIG. 9A.

FIG. 9C is a front view of the toothbrush of FIG. 8 at rest on the tooth surface.

DETAILED DESCRIPTION OF THE INVENTION

Figure 1:
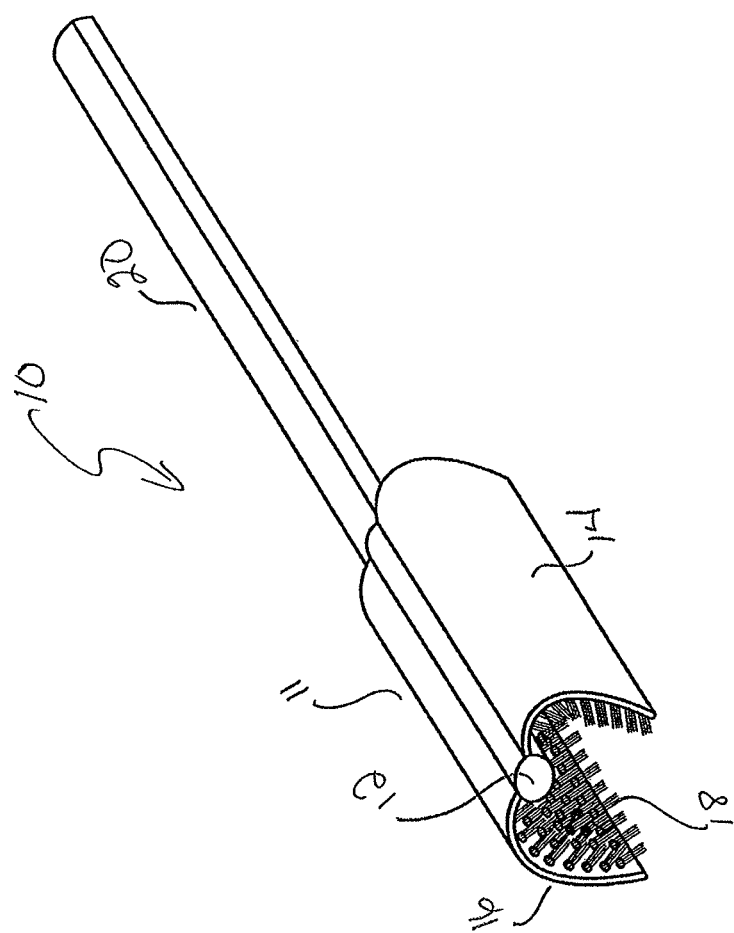
FIG. 1 is a perspective view of an exemplary embodiment of the toothbrush in accordance with the invention.
Figure 3A:
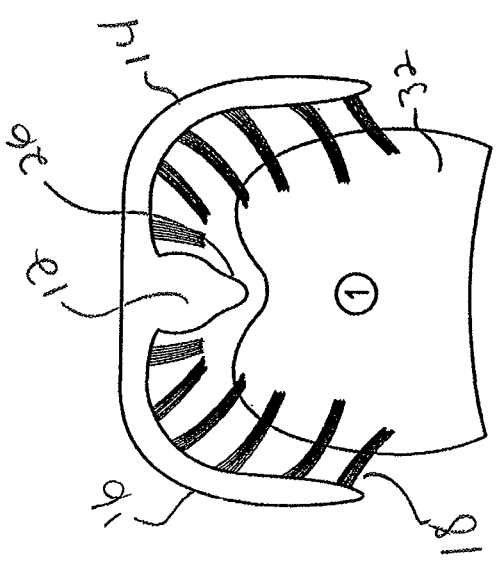
FIGS. 3A-3D are illustrations of an exemplary embodiment of the toothbrush in accordance with the invention depicting the cleaning of a second type of tooth.
Figure 3B:
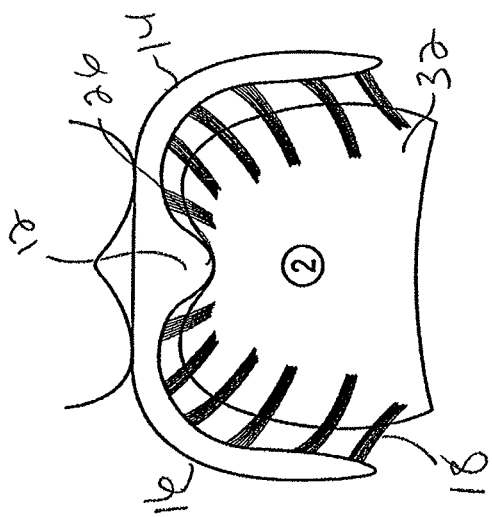
Figure 3C:
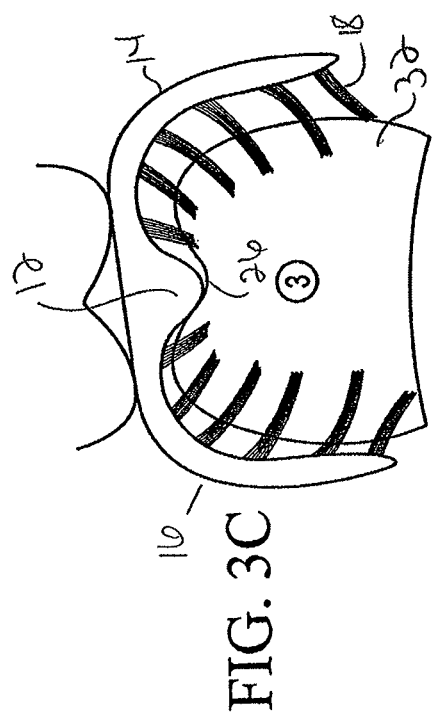
Figure 3D:
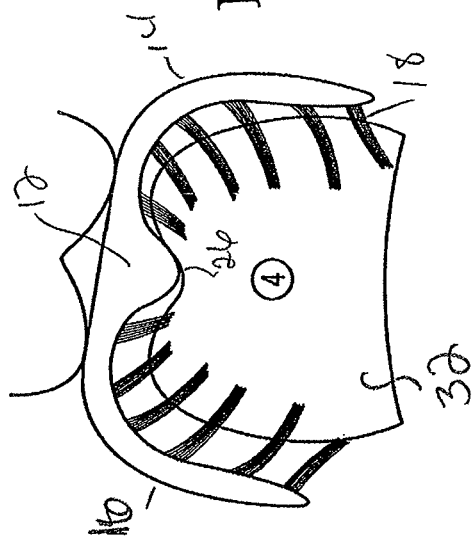

Unless defined otherwise, all technical and scientific terms used herein have the same meaning as is commonly understood by one of skill in the art to which this invention belongs.

Referring now to FIGS. 1 through 7 a first embodiment of a toothbrush in accordance with the invention will be described. Toothbrush 10 includes head portion 11 and optional handle 20. Head portion 11 includes pivot bar 12, flexible anchor portions 14, 16, and a plurality of bristles 18.

Figure 4:
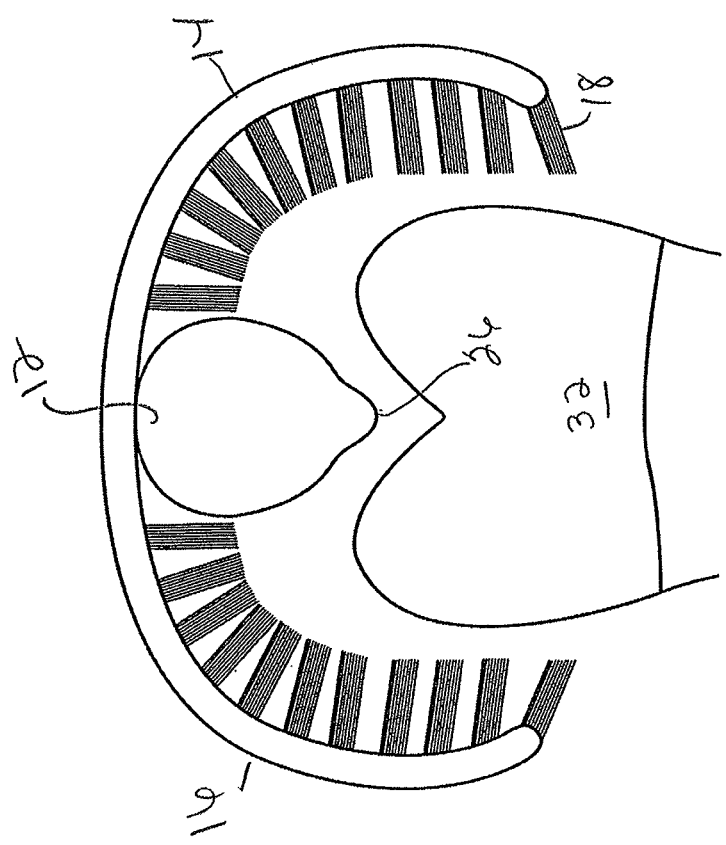
FIG. 4 is a front view of an exemplary embodiment of the toothbrush in accordance with the invention.
Figure 5:
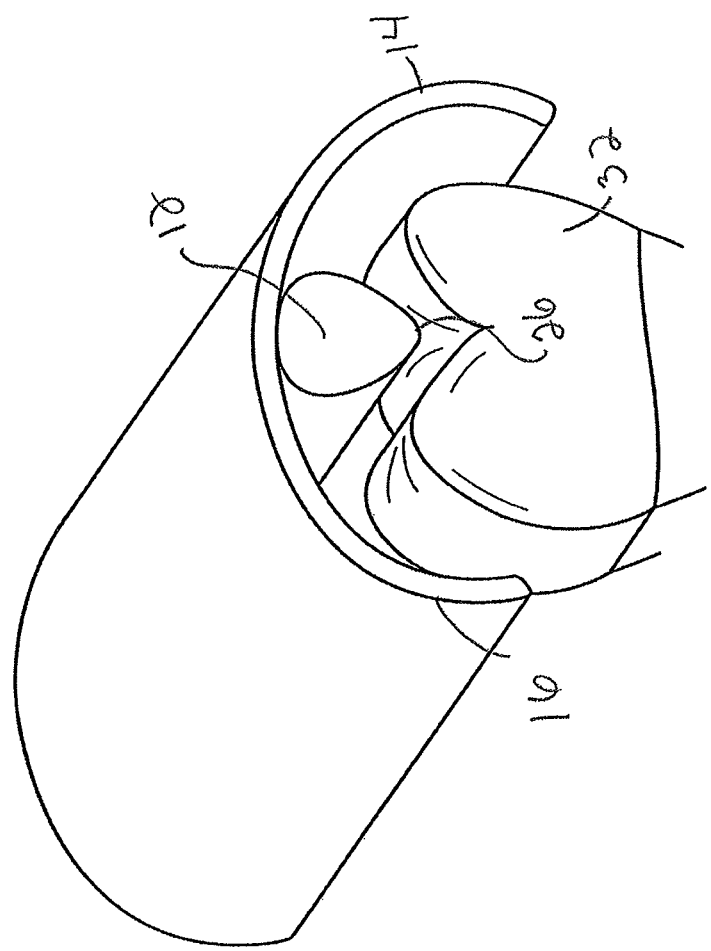
FIG. 5 is a perspective view of the toothbrush in accordance with the invention showing the bristle anchor and pivot bar without bristles.
Figure 6:
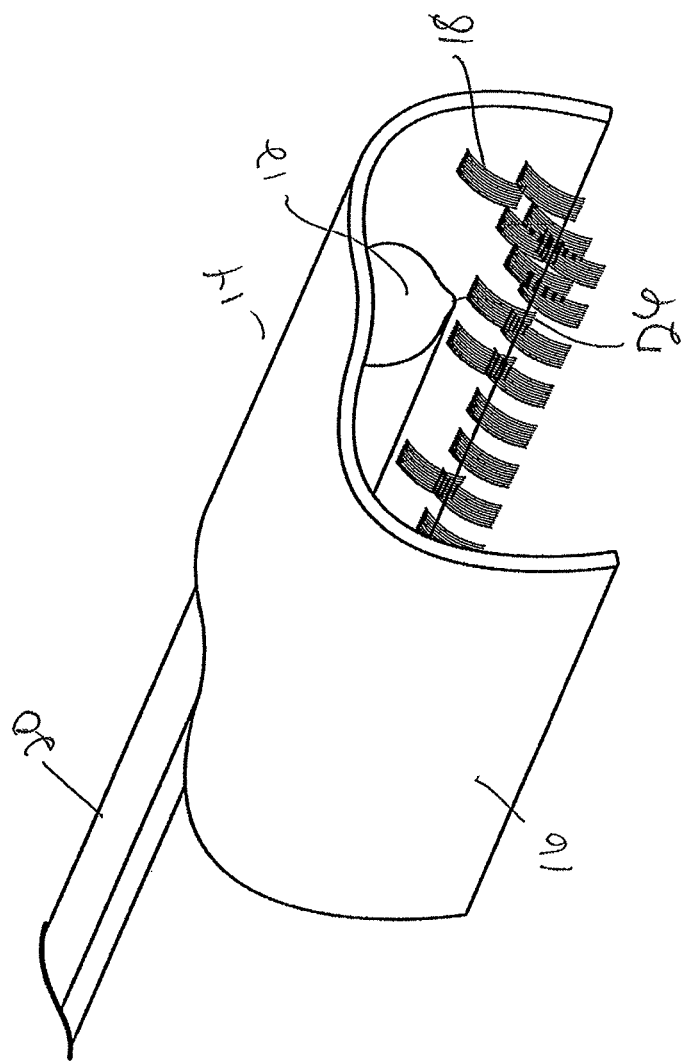
FIG. 6 is a perspective view of the toothbrush in accordance with the invention showing the bristle anchor and pivot bar with some of the bristles.
Figure 7:
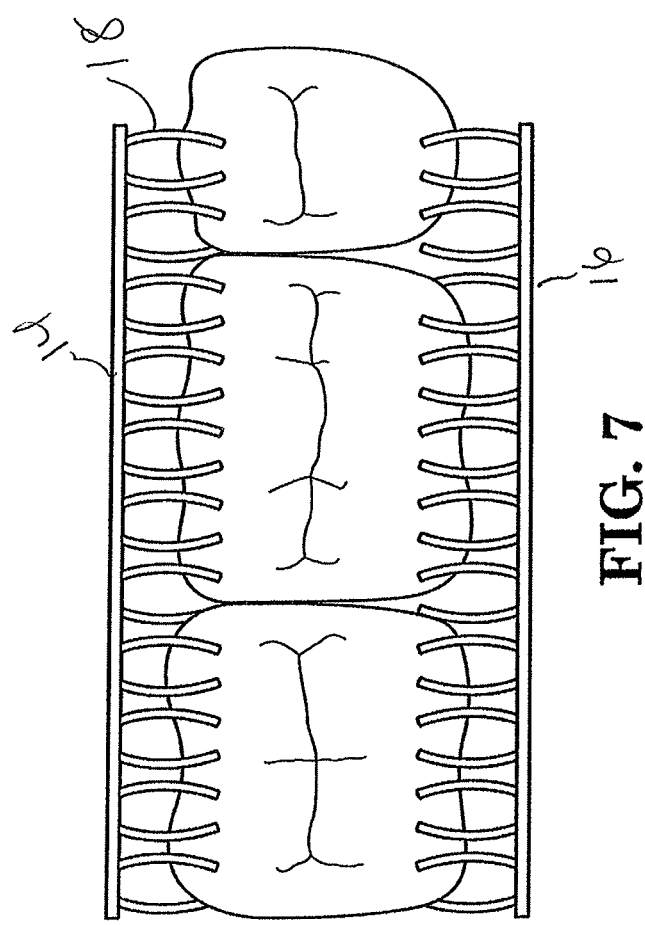
FIG. 7 is a top plan view of the toothbrush in accordance with the invention showing the bristles cleaning teeth.

Flexible anchor portions 14, 16 may be integrally formed (as seen in FIG. 4) or may be constructed as two separate portions as seen in FIG. 1. In the case where the flexible anchor portions 14, 16 are integrally formed pivot bar 12 is operably coupled to anchor portions 14, 16 on the underside surface as best seen in FIG. 4. Alternatively, as best seen in FIG. 1 anchor portions 14, 16 may be operably coupled to opposing sides of pivot bar 12. Pivot bar 12 and anchor portions 14, 16 may be constructed from the same flexible material or different flexible materials so long as they are substantially pliable as the cleaning action occurs. Flexible anchor portions 14, 16 are preferably formed from a pliable or flexible material that allows anchor portions 14, 16 to be compressed when chewed. Flexible materials may include suitable plastics, rubber, nylon, composites, and other similar material. The hardness, resiliency, elasticity, tensile strength, and other physical properties of the flexible anchor portions 14, 16 may be selected according to the particular need and/or application desired.

Anchor portions 14, 16 are formed such that they initially have an uncompressed shape as best seen in FIGS. 1 and 4. Although the shape of anchor portions 14, 16 may vary depending on the design of the toothbrush, the example embodiments utilize an oblong, substantially C-shaped in cross-section anchor. Anchor portions 14, 16 in conjunction with pliable pivot bar 12 are structured to compress against the tooth surface in response to the application of an external force such as chewing and to return to the uncompressed shape in response to removal of the external or chewing force.

As best seen in FIGS. 2A-2C and 3A-3D the anchor portions 14, 16 are shown in various stages of a deformed or compressed shape resulting from the application of an external chewing force by a user. Pivot bar 12 is contoured and adapted to fit the tooth surface in particular the central groove of the molars as best seen in FIGS. 3A-3D, which then guides the other portions of the toothbrush into place on the tooth surface. Pivot bar 12 includes contoured side portions 22, 24 and pointed end portion 26. As seen in FIGS. 2A-2C, sides portions 22, 24 of pivot bar 12 conform to the surface of an incisor, canine or pre-molar tooth 28 and are designed to move along it as the bristles clean the tooth. Pivot bar 12 advantageously allows the anchor portions 14, 16 to pivot or rock back and forth on the tooth surface.

During the cleaning action, opposing incisor, canine or pre-molar tooth 30 contacts the outer surface of anchor portions 14, 16.

FIGS. 3A-3D depict the toothbrush in accordance with the invention cleaning a molar 32. The anchor portions 14, 16 are shown in various stages of a deformed or compressed shape resulting from the application of an external chewing force by a user. Pointed end portion 26 of pivot bar 12 is adapted to engage the central groove in the molar tooth surface. As seen in FIGS. 3A-3D side portions 22, 24 of pivot bar 12 conform to the outer molar surface and are designed to compress to allow bristles 18 to clean the tooth surface. A best seen in FIG. 3B, pivot bar 12 also compresses in response to the chewing force of a user and advantageously pivots from one side to another to allow the anchor portions 14, 16 to compress and pivot along the tooth surface.

Pivot bar 12 together with anchor portions 14, 16 are structured to compress in response to the application of an external force such as chewing and to return to the uncompressed shape in response to removal of the external chewing force. The pivot bar 12 self-guides the toothbrush into place on the various tooth surfaces and, as herein before disclosed, are designed to flex and compress during the chewing process. Pivot bar 12 may optionally include small bristles of a high stiffness that during the chewing process contact the susceptible grooves of the teeth and clean the deep fissures.

The bristles 18 can be attached to anchor portions 14, 16 in any suitable manner known to those of skill in the art. For example, bristles 18 may be molded into anchor portions 14, 16, inserted and bonded into holes formed in anchor portions 14, 16, or the like. In some aspects of the invention, bristles 18 may be located in a random manner or in a specific pattern suited to the shape, size, or application of toothbrush 10. For example, in one aspect, the plurality of bristles 18 may include varying sizes of bristles short, medium length and long, each with varying degrees of stiffness, i.e. low, intermediate or high. In this way, short bristles may act as the first layer of bristles, which are applied to the users gum line. In use, the chewing motion causes the short bristles to gently push against and massage the gum line, thus removing foreign material and plaque from the gum line. A plurality of medium length bristles of intermediate stiffness may act as the second layer of bristles that clean plaque and debris below the gum line and reach in the crevices located between the teeth. The layer of intermediate bristles may also function to clean the overall surface of each tooth and the gums. Long bristles of high stiffness may clean and stimulate the bottom and roof of the mouth and the tongue. For purposes of illustration only, FIGS. 1A through 4 show a small number of bristles of the same apparent length, however the toothbrush in accordance with the invention may include a larger number of densely arranged bristles 18 of varying lengths as herein described. The novel design of the toothbrush allows bristles that are much stiffer than conventional toothbrushes to be used. Stiffer bristles clean better and may be placed strategically in the anchor portions 14, 16 without risk of injury to the root and gums.

The resiliency of the anchor portions 14, 16 and pivot bar 12 changes the angle of the bristles 18 with every bite. As best seen in FIGS. 2A through 3D, in response to the chewing motion, the bristles 18 move and "pinch down" upon the teeth and gums to loosen and remove foreign particles. The different bristle lengths and different bristle stiffness, combined with the compression of anchor portions 14, 16 and pivot bar 12 during chewing, which in turn stimulates the gums and mouth in an unconventional manner. All tooth surfaces may be cleaned in one chewing motion without the risk of causing abrasion of the tooth or recession of the gum line that typically occurs when manual force is used.

Optional handle 20 may be removable or integrally formed with head portion 11. The handle may be constructed as a short finger handle or an extended hand-graspable handle.

Figure 8:
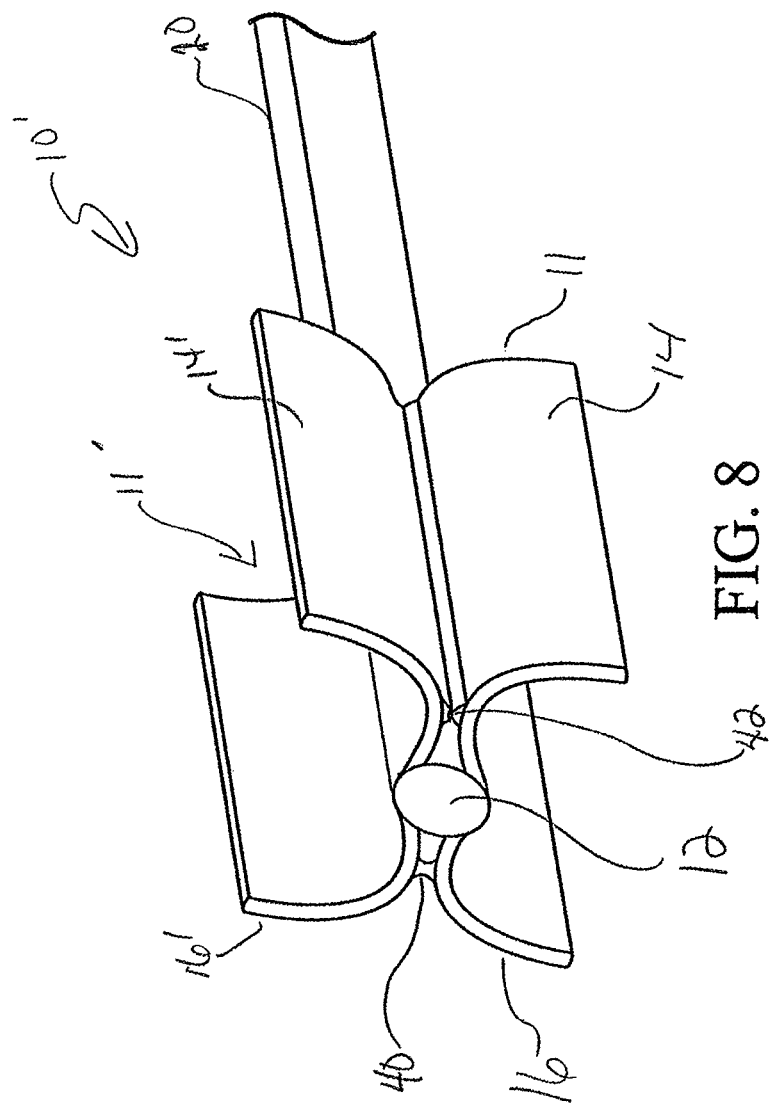
FIG. 8 is a perspective view of another aspect of the toothbrush in accordance with the invention.

FIGS. 8 and 9A through 9C illustrate a second embodiment of the present invention 10' which includes two opposing head portions 11, 11', single pivot bar 12, flexible anchor portions 14, 14' 16, 16', plurality of bristles 18, 18' and optional handle 20. For purposes of illustration only, FIG. 8 depicts the toothbrush 10' without bristles 18. As can be seen opposing head portions 11, 11' are operably coupled by articulating joints 40, 42.

As can be best seen in FIG. 9B articulating joint 40, 42 comprises a ball and socket joint 44. Ball 46 is pivotally received in socket 48. FIG. 9A depicts head portions 11, 11' in the uncompressed positions. As the user chews on pivot portion 12, pivot portion compresses allowing head portions 11, 11' to articulate as ball 46 pivotally rotates in socket 48.

Although the present invention has been described with reference to certain aspects and embodiments, those of ordinary skill in the art will appreciate that changes may be made in form and detail without departing from the spirit and scope of the invention.

What is claimed is:

1. A toothbrush comprising:
    first and second flexible anchor portions extending along a longitudinal axis and away from the longitudinal axis in a first direction that is perpendicular to the longitudinal axis;
    a plurality of bristles coupled to said first and second flexible anchor portions;
    a soft pivot bar longitudinally aligned with the longitudinal axis and operably coupled to said flexible anchor portions, the soft pivot bar including a tooth-engaging portion that extends in the first direction and into a cavity formed between the first and second flexible anchor portions, a cross-sectional shape of the tooth-engaging portion taken in a plane that is perpendicular to the longitudinal axis tapers to a pointed end portion; and
    a plurality of bristles extending from the tooth-engaging portion of the soft pivot bar;
    wherein a chewing force applied to said pivot bar causes said pivot bar and said anchor portions to compress against a tooth surface to cause a cleaning action.

2. The toothbrush according to claim 1, wherein the first and second flexible anchor portions each extend from the soft pivot bar.

3. The toothbrush according to claim 2, wherein each of the first and second flexible anchor portions includes a proximal end that is attached to the soft pivot bar.

4. The toothbrush according to claim 3, wherein a cross-sectional shape of each of the first and second flexible anchor portions, which is taken in a plane that is perpendicular to the longitudinal axis, is concave.

5. The toothbrush according to claim 4, wherein each of the first and second flexible anchor portions includes a distal end that is displaced in the first direction from the soft pivot bar.

6. The toothbrush according to claim 5, wherein a length of the soft pivot bar measured along the longitudinal axis is longer than a depth to which the soft pivot bar extends into the cavity.

7. The toothbrush according to claim 5, wherein:
    the first and second flexible anchor portions and the plurality of bristles form a first head portion; and
    the toothbrush comprising a second head portion including third and fourth flexible anchor portions extending along the longitudinal axis and extending from the soft pivot bar, and a plurality of bristles attached to the third and fourth flexible anchor portions.

8. The toothbrush according to claim 7, wherein the third and fourth flexible anchor portions respectively form a mirror image of the first and second flexible anchor portions about a plane that extends through the longitudinal axis.

9. The toothbrush according to claim 7, further comprising a ball and socket joint formed between the first and second head portions.

10. The toothbrush according to claim 9, wherein the ball and socket joint comprises a socket attached to the first head portion and a ball attached to the second head portion that is received within the socket.

* * * * *